US006766802B1

United States Patent
Keropian

(10) Patent No.: US 6,766,802 B1
(45) Date of Patent: Jul. 27, 2004

(54) SLEEP APPLIANCE

(76) Inventor: Bryan Keropian, 18607 Ventura Blvd., #206, Tarzana, CA (US) 91356

( * ) Notice: Subject to any disclaimer, the term of this patent is extended or adjusted under 35 U.S.C. 154(b) by 0 days.

(21) Appl. No.: 10/456,034

(22) Filed: Jun. 5, 2003

(51) Int. Cl.[7] ................................................ A61F 5/56
(52) U.S. Cl. ........................ 128/848; 602/902; 128/859
(58) Field of Search ........................ 128/848, 859–862; 602/902; 433/6, 7, 8

(56) References Cited

U.S. PATENT DOCUMENTS

| 2,705,006 | A |   | 6/1955  | Cettel et al. |        |
|-----------|---|---|---------|---------------|--------|
| 3,277,892 | A | * | 10/1966 | Tepper        |        |
| 4,273,530 | A | * | 6/1981  | Broussard     | 433/6  |
| 4,299,568 | A | * | 11/1981 | Crowley       | 433/6  |
| 4,468,196 | A | * | 8/1984  | Keller        | 433/7  |
| 4,669,459 | A |   | 6/1987  | Spiewak et al.|        |
| 4,676,240 | A |   | 6/1987  | Gardy         |        |
| 4,901,737 | A | * | 2/1990  | Toone         | 128/848|
| 4,976,614 | A | * | 12/1990 | Tepper        | 433/6  |
| 5,096,416 | A | * | 3/1992  | Hulsink       | 433/6  |
| 5,376,001 | A | * | 12/1994 | Tepper        | 433/6  |
| 5,580,243 | A | * | 12/1996 | Bloore        | 433/6  |
| 5,607,300 | A | * | 3/1997  | Tepper        | 433/6  |
| 6,467,484 | B1|   | 10/2002 | De Voss       |        |
| 2001/0027793 | A1 |   | 10/2001 | Tielemans |        |
| 2002/0189620 | A1 |   | 12/2002 | L'Estrange et al. | |

* cited by examiner

Primary Examiner—Michael A. Brown
(74) Attorney, Agent, or Firm—Sanford Astor

(57) ABSTRACT

A dental oral appliance for use with patients who suffer with sleep disorders, to reduce or eliminate snoring and to open the airway for a sleeping individual who suffers with obstructive sleep apnea. The appliance covers the inside (lingual) of the upper teeth and has an open palate. Retention for the appliance is provided by clasps placed over the upper right and left molars and a retainer in the anterior area from cuspid to cuspid. Over the upper central incisors is a raised strip that extends from the incisal tip (biting edge) of the central incisors toward the lingual. It extends back from the middle of the central incisors, where they meet or touch each other, to the middle of the palate. This raised anterior area is to separate the posterior teeth to reduce spasm on the temporalis muscle. There is a transverse strip that extends from the inside (lingual) of the upper right molars to the inside of the upper left molars which covers the tongue, holding it down, opening the airway.

20 Claims, 3 Drawing Sheets

SLEEP APPLIANCE

BACKGROUND OF THE INVENTION

It has been estimated that ninety million American adults and children snore and that one in every ten adults snores. Snoring can have serious medical consequences for some people. Snoring is the first indication of a potentially life-threatening sleep disorder called Obstructive Sleep Apnea. If not diagnosed or if left untreated, Obstructive Sleep Apnea could result in severe medical consequences such as systemic high blood pressure, cardiovascular disease and even sudden death.

Snoring is caused by vibration of the tissues due to air turbulence as the airway narrows and may be a sign that a patient is suffering from apnea. But not all snorers suffer from apnea. Snoring can be categorized by its severity. There is the snorer who snores but experiences no physical problems. Then there is the snorer who suffers from apnea, or the snorer who suffers from upper airway resistance. In some of these people, though they may not actually experience apneic episodes, their snoring is so loud and their breathing so labored, that it still wakes them, and their partners, numerous times throughout the night.

Many spouses, partners and/or children suffer through the night from the annoying noise of the snorer. Snoring not only disturbs the sleeping pattern of the snorer himself, it is also disruptive to the family life by causing lack of sleep to all involved. This leaves all involved unrefreshed, tired and sleepy throughout the day. It can cause sleepiness while driving, reading, working or doing other tasks.

A broad variety of intra-oral and dental appliances and devices are now available to treat a patient for snoring. Some known oral devices for treating snoring and obstructive sleep apnea are worn inside of the mouth and work by repositioning of the jaw, moving the mandible, lifting the soft palate or moving the tongue forward. The various classes of treatment devices that now exist include mandibular advancers and tongue advancers. These appliances work by advancing the tongue and soft palate away from the back wall of the throat. Other methods used to treat snoring include controlled positive air flow pressure systems also known as CPAP which require a nose mask and which are quite uncomfortable.

Other treatments for snoring include various surgeries, which are drastic steps to take to attempt to cure the problem however snoring can be so disruptive to a person's life and relationships, that some sufferers resort to surgery.

Another device which has been known is described in U.S. Pat. No. 6,467,484 to De Voss. The device of De Voss fits entirely over the teeth and presses against the inside of the mouth and the gums, making it uncomfortable for the user to wear. In addition, the device is held in the user's mouth only by pressure against the teeth from the groove in the U-shaped member that fits over the teeth. If that pressure releases for any reason, such as material fatigue, the entire device can fall off of the teeth, which could be a very dangerous situation.

BRIEF DESCRIPTION OF THE INVENTION

The sleep appliance of this invention is a dental oral appliance for use with patients who suffer with sleep disorders. Primarily it is designed to reduce or eliminate snoring and to open the airway for a sleeping individual who suffers with obstructive sleep apnea.

The appliance is physically designed similar to an upper (maxillary) orthodontic retainer, commonly called a Hawley retainer. It covers the inside (lingual) of the upper teeth and has an open palate (nothing covering the middle area of the palate.) Retention (holding ability) for the appliance is provided by clasps, commonly called Adams clasps, placed over the upper right and left molars. In the anterior area from cuspid to cuspid, there is a retainer wire that is the standard wire used on orthodontic appliances to hold the anterior teeth in place or to move them backwards (inward towards the palate [lingually]).

In the anterior area over the upper central incisors is a raised strip that extends from the incisal tip (biting edge) of the central incisors toward the lingual. It extends back from the middle of the central incisors (where they meet or touch each other) to the middle of the palate. This raised anterior area is to disclude or separate the posterior teeth. The net effect is to reduce spasm on the temporalis muscle and aid in reducing migraine and chronic tension headache pain that comes from bruxing and clenching (squeezing teeth together with potentially up to thousands of pounds of pressure). Nocturnal bruxing and clenching are the cause of pain coming from the spasmed temporalis muscle.

There is a transverse strip that extends from the inside (lingual) of the upper right molars to the inside of the upper left molars. This transverse strip extends from the right to the left and covers the tongue, holding it down.

To understand the effectiveness of the appliance, the mechanism of snoring and obstructive sleep apnea must be understood. While we sleep, the tongue falls back and up towards the palate and it partially or completely obstructs or closes the path of the airway. This results in snoring, obstructive sleep apnea, or Upper Airway Resistance Syndrome. The medical treatment for these maladies range from medication to a C-PAP (Continuous Positive Airway Pressure) machine. The C-PAP is nearly 100% successful when utilized. Unfortunately, the non-compliance for C-PAP use ranges from 50% to 80% depending where one searches in the literature. The American Association of Sleep Medicine designated dental sleep appliances as the number one alternative to CPAP. The sleep appliance of this invention is designed to treat the problem of tongue blockage when sleeping. It works by utilizing several factors. First, it changes the vertical dimension (height of the opening or separation of the teeth). This results in an increased opening of the airway. Second, the strip that runs transverse along the back of the appliance effectively holds the tongue down and does not allow it to fall back and block the airway opening.

OBJECTS OF THE INVENTION

Accordingly, several objects and advantages of the invention are as follows:

It is an object of this invention to provide a simple device to prevent or reduce snoring as well as Obstructive Sleep Apnea.

It is another object of this invention to provide a device, easily applied and easily tolerated, which will substantially prevent snoring.

Further objects and advantages will become apparent from a consideration of the following description and drawings.

DETAILED DESCRIPTION OF THE INVENTION

Figure 1:
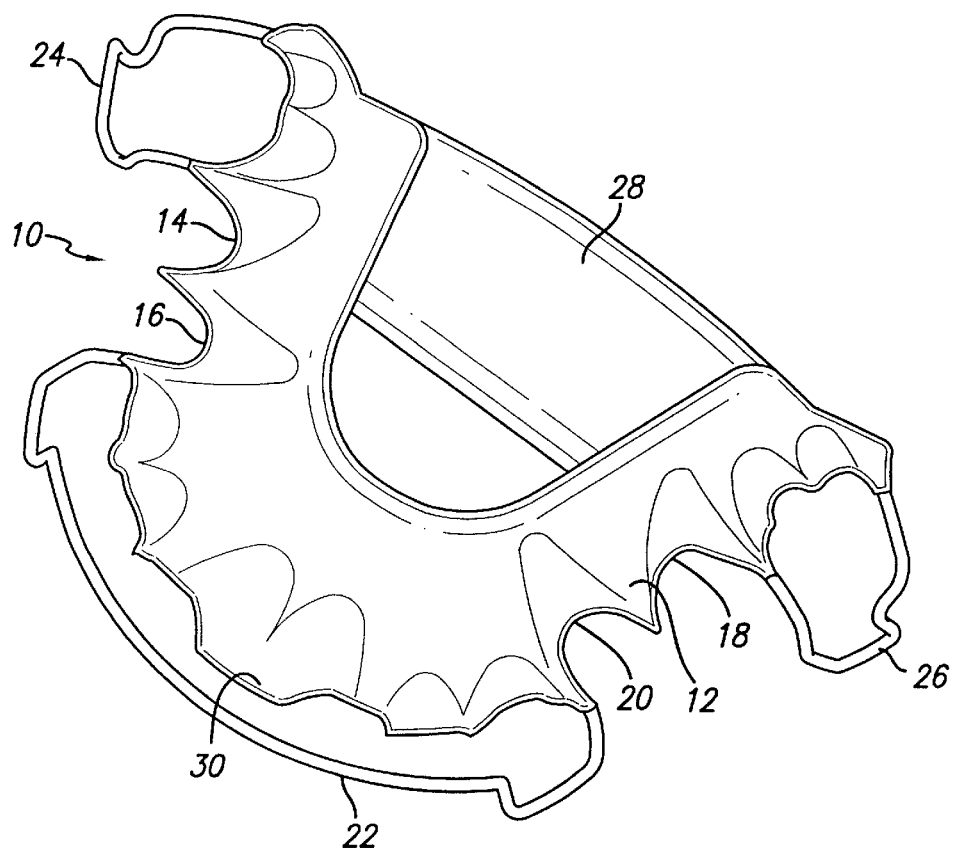
FIG. 1 is a perspective view of the sleep appliance of this invention.
Figure 2:
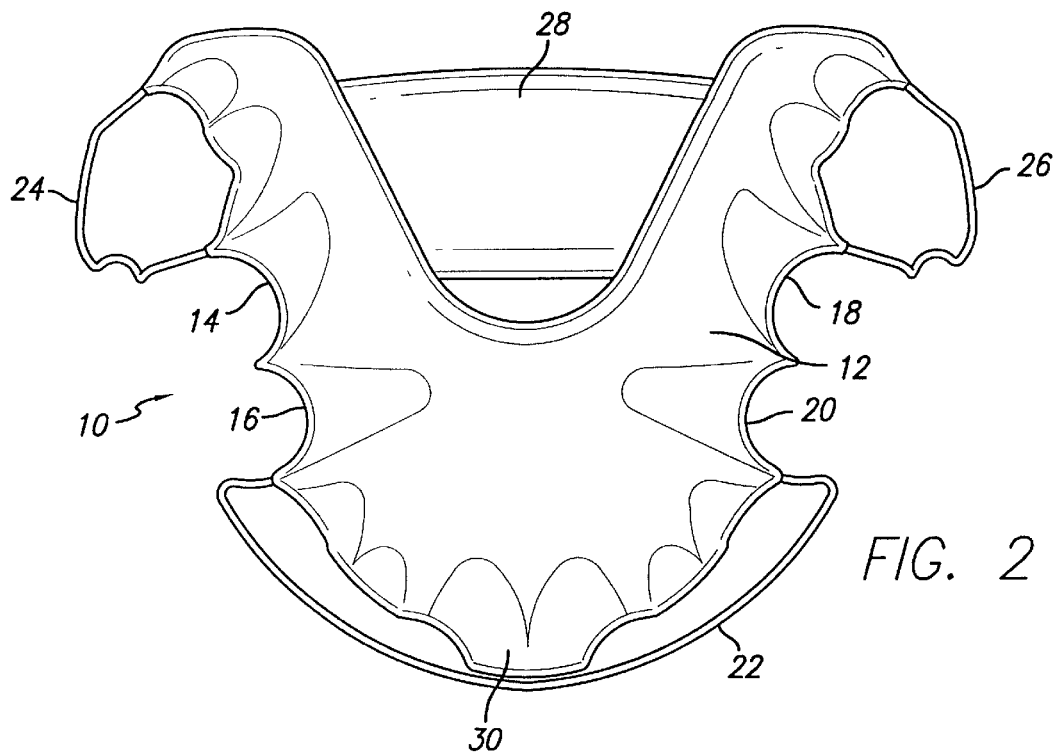
FIG. 2 is a top view.
Figure 3:
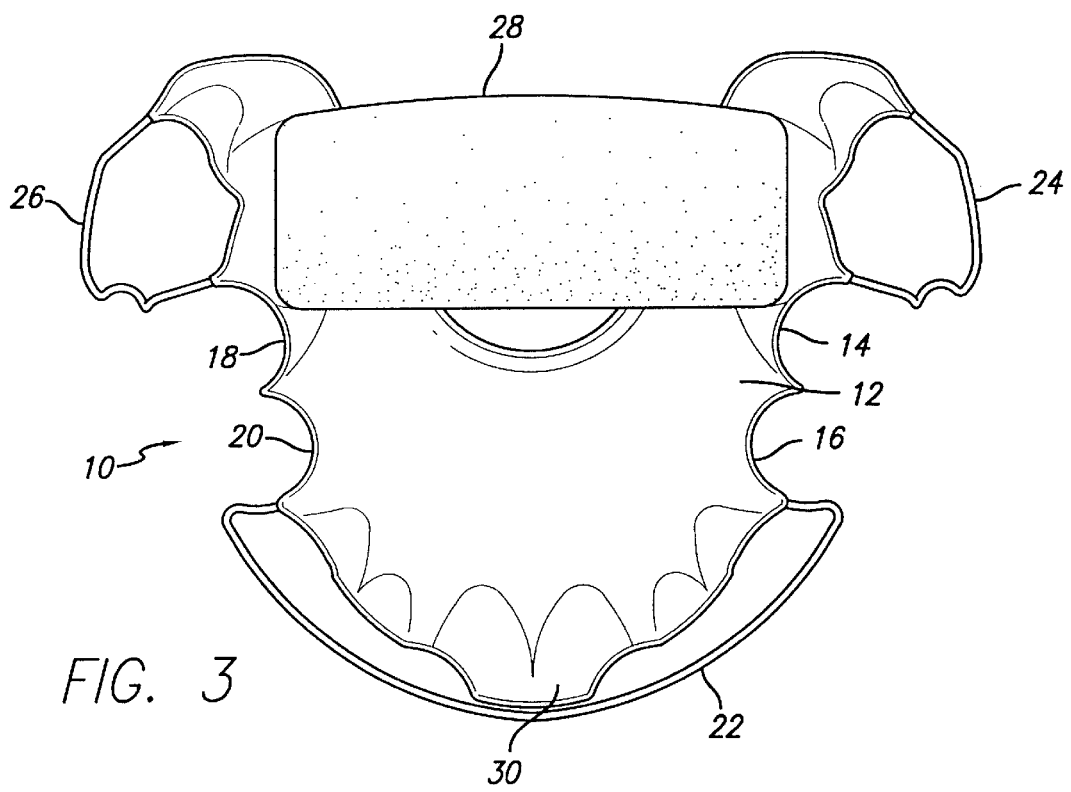
FIG. 3 is a bottom view.

Referring now to FIGS. 1, 2 and 3, there is shown the sleep appliance of this invention. It comprises body 12 which fits adjacent the inside of the upper teeth of the person wearing it. Body 12 fits snugly against the palate, or roof of the mouth. Body 12 is generally U-shaped, however it has a series of recesses 14,16, 18 and 20, as well as additional recesses as needed, to fit the body 12 against the lingual side of the upper teeth, covering the inside of the upper teeth. The device is custom fit to each patient by making a mold or dental impression of the inner surface of the upperteeth and the palate. The appliance is then made from the mold using a clear acrylic plastic commonly used for dental appliances.

Appliance 10 is held in place by an anterior retainer 22 and two posterior retaining clasps 24 and 26. Anterior retainer 22 is a wire, usually made of metal and extends from eye-tooth to eye-tooth, #6–#11. Retainer wire 22 is similar to the standard wire used on orthodontic appliances to hold the anterior teeth in place or to move them backwards, inward ([lingually) towards the palate. These wires are usually made of stainless steel.

Appliance 10 is further held in place by two posterior retaining clasps 24 and 26, commonly called Adams clasps, placed over upper right and left molars, preferably the first molars. Clasps 24 and 26 are also wires, usually made of metal, and usually stainless steel. Retainer wires 22, 24 and 26 hold appliance 10 securely in place.

Transverse strip 28 extends from the inside (lingual) of the upper right molars to the inside of the upper left molars, preferably the second molars. Transverse strip 28 extends from the right to the left side of appliance 10, covering the tongue, acting as a tongue depressor, holding down the tongue, leaving an open air passage.

In the anterior area over the upper central incisors there is a raised incisor strip 30 that extends from the incisal tip (biting edge) of the central incisors toward the lingual. Strip 30 extends back from the middle of the central incisors, where they meet or touch each other, to the middle of the palate. This raised strip acts as a bite discluder, separating the posterior teeth, which reduces spasm on the temporalis muscle and aids in reducing migraine and chronic tension and headache pain, which come from a spasmed temporalis muscle.

Strip 30 is preferably from about 3 mm to about 5 mm thick in order to separate the posterior teeth. Body 12, tongue depressor 28 and strip 30 are preferably made of a clear acrylic plastic commonly used for dental appliances, but could be made from other plastics or rubber material.

Figure 4:
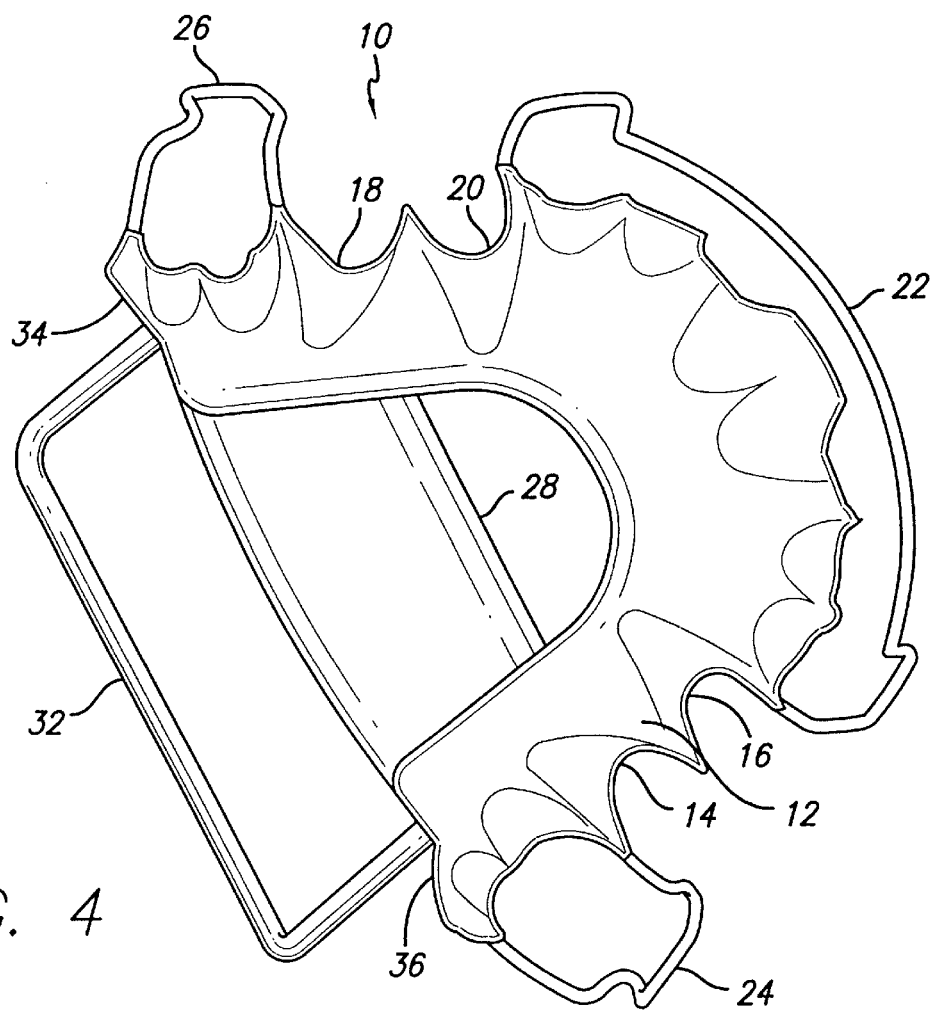
FIG. 4 is a perspective view of another embodiment.
Figure 5:
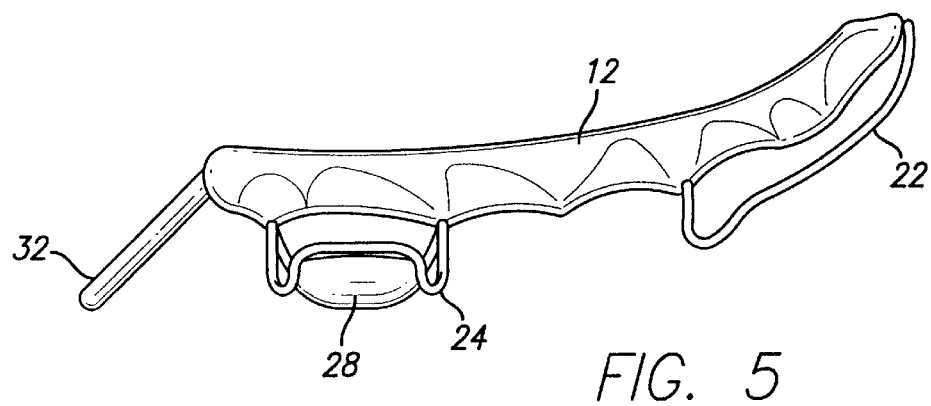
FIG. 5 is a side view of the embodiment shown in FIG. 4.

In another embodiment shown in FIGS. 4 and 5, sleep appliance 10 is exactly the same as the embodiment shown in FIGS. 1–3, except that an additional transverse wire 32 is attached to the back or posterior ends 34 and 36 of body 12. Wire 32 passes transversely across the rear of body 12 and is angled downwardly to act as a further tongue depressor, if necessary. In many instances, transverse strip 28 will be sufficient to hold the tongue down, open the air passage, and substantially prevent snoring. In some instances however, it may be necessary to add an additional second tongue depressor 32 to hold the tongue down even further to obtain the desired result. Tongue depressor 32 is tilted down towards the tongue at an angle to the horizontal of about 30 to 60 degrees, preferably 45 degrees. Tongue depressor 32 is also made of wire, usually stainless steel.

Having thus described the invention, it is requested that the invention be described by the scope of the following claims.

I claim:

1. A dental oral appliance to open the airway for a sleeping individual who suffers with snoring or obstructive sleep apnea comprising, a body portion covering the inside of the upper teeth, said body having an open palate, clasps placed over the upper right and left molars, a retainer in the anterior area from cuspid to cuspid, a raised incisor strip that extends from the incisal tip of the central incisors to the middle of the palate and a plastic or rubber transverse tongue depressor that extends from the inside of the upper right molars to the inside of the upper left molars to hold the tongue down.

2. The device of claim 1 in which the clasps are placed over the right and left first molars.

3. The device of claim 1 in which the body has a series of recesses to fit against the lingual side of the upper teeth.

4. The device of claim 1 in which the retainer and clasps are made from metal wire.

5. The device of claim 4 in which the metal wire is stainless steel.

6. The device of claim 1 in which the body and tongue depressor are made of clear epoxy plastic.

7. The device of claim 1 in which the clasps are Adams clasps.

8. A dental oral appliance to open the airway for a sleeping individual who suffers with snoring or obstructive sleep apnea comprising, a body portion covering the inside of the upper teeth, said body having an open palate, clasps placed over the upper right and left molars, a retainer in the anterior area from cuspid to cuspid, a raised incisor strip that extends from the incisal tip of the central incisors to the middle of the palate and a transverse tongue depressor that extends from the inside of the upper right molars to the inside of the upper left molars to hold the tongue down, a second transverse tongue depressor attached to the back of the body and angled down towards the tongue.

9. The device of claim 8 in which the second tongue depressor is angled towards the tongue at an angle of from about 30 degrees to about 60 degrees.

10. The device of claim 8 in which the second tongue depressor is made of stainless steel.

11. A dental oral appliance to open the airway for a sleeping individual who suffers with snoring or obstructive sleep apnea comprising, a body portion adjacent the inside of the upper teeth, said body having an open palate and a series of recesses to fit against the lingual side of the upper teeth, clasps placed over the upper right and left first molars, a retainer in the anterior area from cuspid to cuspid, a raised incisor strip that extends from the incisal tip of the central incisors to the middle of the palate to separate the posterior teeth and a plastic or rubber transverse tongue depressor that extends from the inside of the upper right molars to the inside of the upper left molars to hold the tongue down.

12. The device of claim 11 in which the retainer and clasps are made from metal wire.

13. The device of claim 12 in which the metal wire is stainless steel.

14. The device of claim 11 in which the body and tongue depressor are made of clear epoxy plastic.

15. The device of claim 11 in which the clasps are Adams clasps.

16. The device of claim 1 or 11 in which the body portion is custom fit to each patient.

17. The device of claim 1 or 11 in which the transverse tongue depressor is made of clear acrylic plastic.

18. A dental oral appliance to open the airway for a sleeping individual who suffers with snoring or obstructive sleep apnea comprising, a body portion adjacent the inside of the upper teeth, said body having an open palate and a series of recesses to fit against the lingual side of the upper teeth, clasps placed over the upper right and left first molars, a retainer in the anterior area from cuspid to cuspid, a raised incisor strip that extends from the incisal tip of the central incisors to the middle of the palate to separate the posterior teeth and a transverse tongue depressor that extends from the inside of the upper right molars to the inside of the upper left molars to hold the tongue down, a second transverse tongue depressor attached to the back of the body and angled down towards the tongue.

19. The device of claim 18 in which the second tongue depressor is angled towards the tongue at an angle of from about 30 degrees to about 60 degrees.

20. The device of claim 18 in which the second tongue depressor is made of stainless steel.

\* \* \* \* \*